United States Patent [19]

Doyle

[11] Patent Number: 5,054,869

[45] Date of Patent: Oct. 8, 1991

[54] LIGHT PIPE SYSTEM HAVING MAXIMUM RADIATION THROUGHPUT

[75] Inventor: Walter M. Doyle, Laguna Beach, Calif.

[73] Assignee: Axiom Analytical, Inc., Laguna Beach, Calif.

[21] Appl. No.: 487,601

[22] Filed: Mar. 2, 1990

[51] Int. Cl.⁵ .............................................. G02B 6/00
[52] U.S. Cl. ................................... 385/133; 385/125; 385/147
[58] Field of Search ............... 350/96.10, 96.15, 96.20, 350/96.28, 96.29, 96.30, 96.32

[56] References Cited

U.S. PATENT DOCUMENTS

| | | | |
|---|---|---|---|
| 3,998,591 | 12/1976 | Eckfeldt | 350/96.32 X |
| 4,029,391 | 6/1977 | French | 350/96.10 X |
| 4,305,640 | 12/1981 | Cullis et al. | 350/96.10 |
| 4,411,490 | 10/1983 | Daniel | 350/96.10 |
| 4,420,690 | 12/1983 | Kuehl | 356/246 X |
| 4,496,211 | 1/1985 | Daniel | 350/96.20 |
| 4,730,882 | 3/1988 | Messerschmidt | 350/96.10 |

OTHER PUBLICATIONS

Ohlmann et al., "Far Infrared Transmission Through Metal Light Pipes", *J.O.S.A.*, vol. 48, No. 8, Aug. 1958, pp. 531–533.

*Primary Examiner*—John D. Lee
*Attorney, Agent, or Firm*—Thomas J. Plante

[57] ABSTRACT

A radiation guiding structure for incoherent radiation is disclosed in which a collimated beam is transmitted through a light pipe having high radition throughput. Radiation losses due to absorbance are minimized by: (1) matching the area of the beam and the light pipe passage; (2) minimizing the number of reflectances of a given ray by reducing the angular divergence of radiation in the beam; and (3) using a reflective coating on the wall of the light pipe which has the low point of its reflectance curve at a relatively high grazing angle.

17 Claims, 8 Drawing Sheets

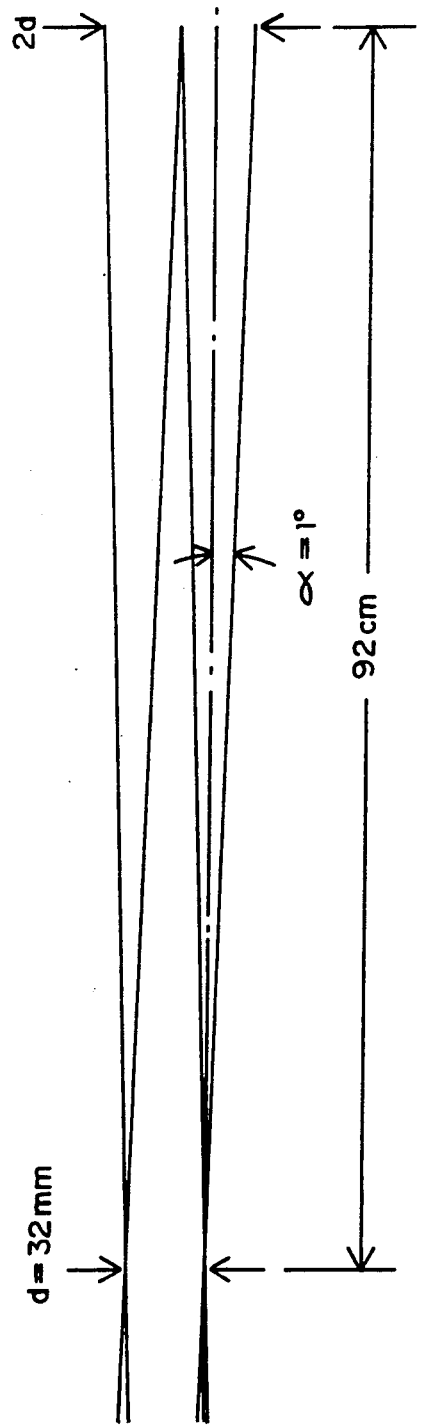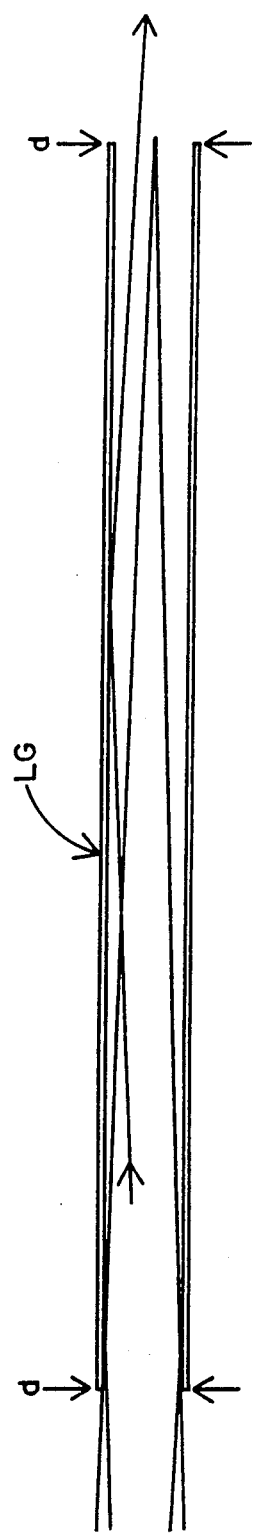

LIGHT PIPE SYSTEM HAVING MAXIMUM RADIATION THROUGHPUT

This invention relates to light pipes, through which incoherent radiation (radiation other than lasers) may be transmitted a substantial distance with minimum radiation loss. The primary field of intended use is mid-infrared light transmission in analytical instruments, such as spectrometers. However, numerous other uses may occur.

Heretofore, light pipes have not been considered very useful for maximizing light transmission. Rather, they have been used to provide light confinement. For example, laser radiation may be enclosed in light pipes to protect workers from high energy radiation.

Also, light pipes have been used to prevent ambient light from combining with the light being used for analysis, and to prevent ambient air from interfering with that light. The latter purposes appear to be those desired in the disclosure of FIG. 2 of U.S. Pat. No. 4,730,882. In most of such light pipe uses, the radiation is focused as it enters the light pipe. The result is a large number of reflections of the rays at the sides of the light pipe, which cause large radiation losses because of the absorption at each point of reflection.

Light guides, in the form of fiber optics, have been very useful in the transmission of visible and near-infrared radiation. Recently, there has been much interest in the possible use of fiber optics in the mid-infrared range to convey information from a spectrometer to a measurement site and back. However, attempts to do this have not been successful for two reasons. First, fibers have yet to be produced which exhibit adequate transmission in the mid-infrared spectral ranges of interest. Second, and more important, mid-infrared detectors are much less sensitive than visible and near-infrared detectors. This means that the optical system must have a very high throughput (i.e., the product of area times solid angle field of view at any point in the system). This in turn would require the use of relatively large diameter and hence stiff fibers.

Light guides, in the form of pipes having highly reflective internal surfaces, will transmit mid-infrared radiation. However, the conventional wisdom is that such light pipes are too lossy (highly absorbing) to be useful as general purpose transmission means for mid-infrared. This belief is based partly on experience and partly on theory. For example, workers designing GC/IR (gas chromatograph infrared) light pipes have noted that the transmitted signal level falls off rapidly with length to diameter ratios exceeding 100 or 200.

Although various limited uses of light pipes have occurred, in the instances known to applicant they have, as in U.S. Pat. No. 4,730,882, used a small diameter pipe, and focussed the infrared radiation into the end of the light pipe. With this arrangement, the radiation will cover a range of incidence angles from 90° (grazing) down to typically 70°.

The present application is based on the discovery that light pipes may, in fact, be used quite successfully for reasonably long distance transmission of incoherent radiation, provided certain important principles are followed in designing such light pipes and the systems in which they are incorporated.

SUMMARY OF THE INVENTION

The present invention is based on several concepts, each of which contributes individually to effective light pipe radiation transmission. In combination, a plurality of these concepts will provide synergistic benefits.

(1) A nominally collimated beam is used, which has an area (cross-sectional) substantially equal to the area of the cylindrical passage in the light pipe (or pipes). The cylindrical passage is, of course, as reflective as possible, in order to minimize radiation absorption by the light pipe.

(2) The light pipe is relatively large in diameter, so as to minimize the number of ray reflections per unit of length. This may also be described as a limitation on the length-to-diameter ratio of the light pipe.

(3) The nominally collimated radiation beam should have minimum, and uniform, angular divergence of the rays across the face of the beam. This divergence depends, in part, on the diameter of the detector. Use of a detector which is as small as possible minimizes angular ray divergence, and thus minimizes radiation loss in the light pipe.

(4) A surprising finding is that reflective metallic coating on the interior of the light pipe may provide better throughput with a material which does not have the highest reflectivity, but which has preferred values of "k" (the "imaginary" part of its index of refraction) and "n" (the "real" part of its index of refraction). In particularly, a relatively low value of "n" will move the minimum point on the curve of reflectance-versus-angle to a larger grazing angle. This, in turn, makes it possible to take advantage of the rapid increase in reflectance that takes place as the ray angle approaches grazing incidence.

(5) If the detector diameter is small enough that the maximum divergence angle is smaller than the angle corresponding to the minimum of the reflectance curve (referred to in the preceding paragraph) an improved throughput efficiency can be attained.

(6) Where it is desired to change direction of the collimated beam inside a plurality of light pipes, plane mirror rotary joints are used to couple successive sections of light pipe in such a way as to preserve the coaxial nature of the radiation distribution in the light pipes.

BRIEF DESCRIPTION OF THE DRAWINGS

FIGS. 2A and 2B provide a comparison of radiation throughput without a light pipe and radiation throughput with a light pipe;

DETAILED DESCRIPTION OF THE SPECIFIC EMBODIMENTS

Figure 1:
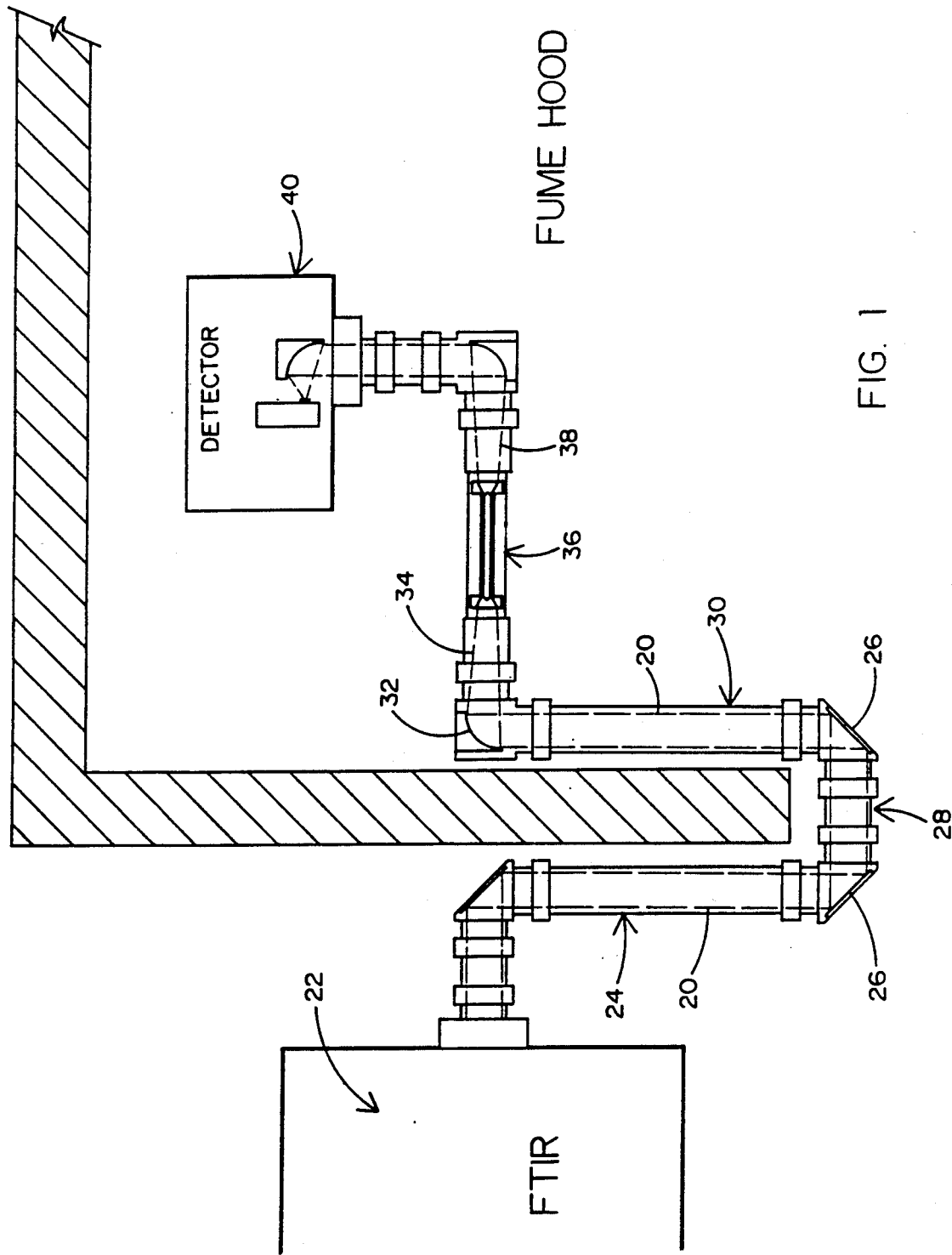
FIG. 1 is a schematic, showing a spectrometer radiation transmission system incorporating light pipes.

FIG. 1 shows an extended light pipe system, in which a collimated radiation beam 20 from a source, e.g., an interferometer 22, enters a first light pipe 24, and is reflected by flat mirrors 26 into second and third light pipes 28 and 30. From light pipe 30, the beam 20 is reflected by a focusing mirror 32 (e.g., a parabolic mirror) so that the converging pre-sample radiation 34 is directed into sample cell 36. Post-sample diverging radiation 38 is directed to a detector 40 by appropriate optics. The nature of the sample does not affect the usefulness of the present invention. The sample cell 36 shown as an example is a liquid-containing chamber in which radiation passes through an internally reflecting element.

The interior walls of light pipes 24, 28 and 30 have highly reflective surfaces, usually provided by a metallic coating. The diameter of collimated beam 20 is substantially identical to the internal diameter of the light pipes 24, 28, and 30. If the beam were perfectly collimated, i.e., coherent, or if the interior surfaces of the light pipes were 100% reflective, radiation loss would not be a problem. But the radiation (which is not coherent) has an angle of diversion which makes it impossible to have all rays traveling parallel to the light pipe walls; and 100% reflectivity (zero absorbance) is not obtainable. As a result, rays in the radiation beam will be reflected from the light pipe walls; and each reflection of a ray will cause a loss of throughput due to absorption of a small percentage of the ray intensity.

Because the light pipe reflections cause throughput loss, it is useful to compare the throughput of a light pipe with the throughput in the absence of a light pipe. The difference is extremely significant. FIGS. 2A and 2B provide an illustration, FIG. 2A illustrating loss of beam intensity without a light pipe, and FIG. 2B illustrating loss of beam intensity with a light pipe. In these figures, the vertical dimensions assume a starting beam diameter d of 32 mm, and a median half angle divergence (alpha) of one degree. With this divergence, the beam will double in diameter to 2 d in 92 cm (in the absence of the light pipe). This results in a reduction of beam intensity by a factor of four (i.e., to 25% of the initial intensity). In the case of a light pipe (LG) with an aluminum coating (FIG. 2B), the one degree median ray will experience an absorbance of 0.072 absorbance units per meter, or 0.066 total absorbance units in 92 cm. This corresponds to an intensity of 86% of the initial value, thus proving the utility of light pipes under these conditions.

Figure 3:
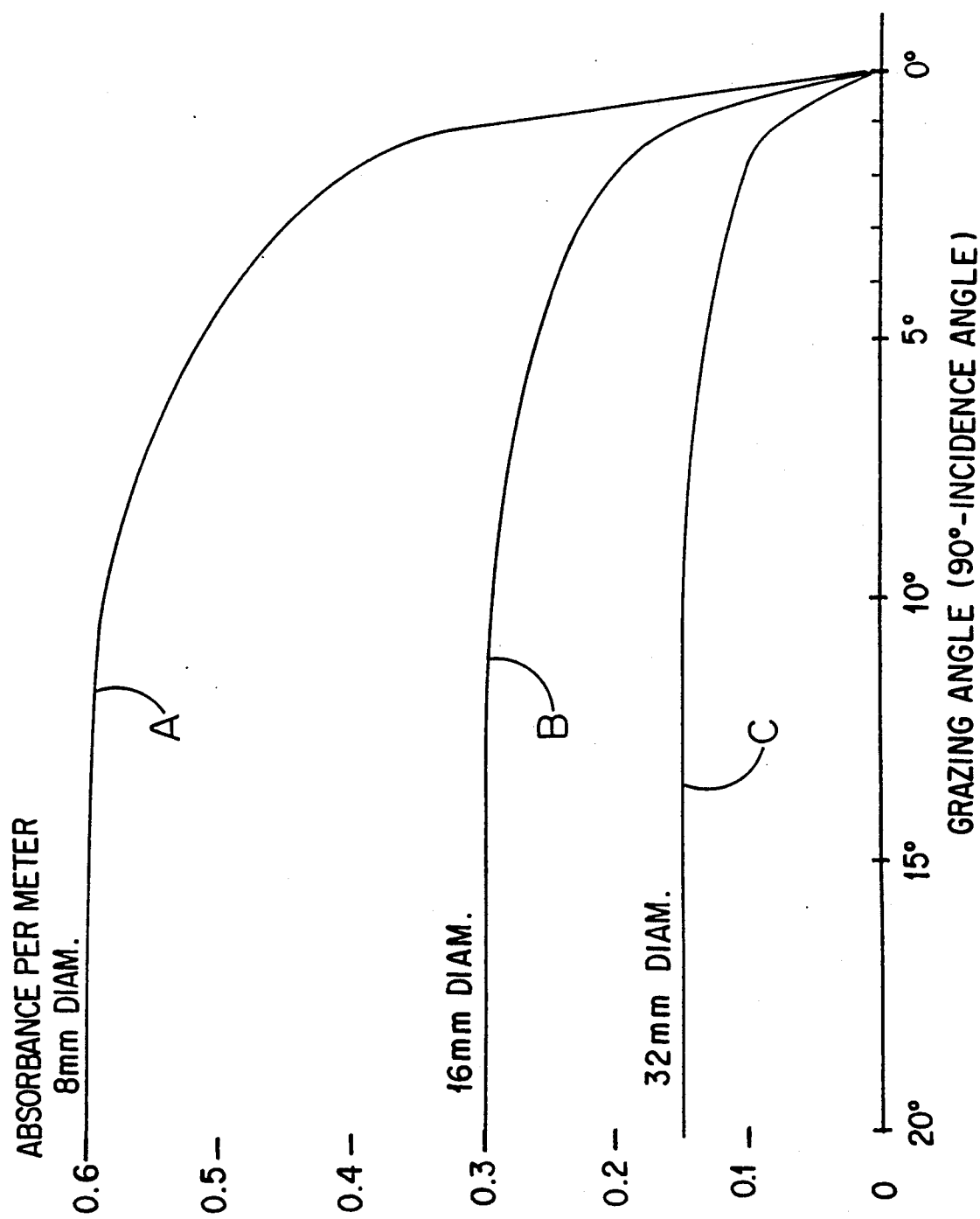
FIG. 3 is a graph showing the relation of radiation absorbance to light pipe diameter.

Having a relatively large diameter of the light pipes will minimize the number of reflections, assuming a given light pipe length. (The light pipe length will be determined by the physical arrangement of the radiation system) The relation of light pipe diameter to absorbance per unit of length is shown graphically in FIG. 3. The X-axis of the graph shows grazing angles ranging from 20° to 0°. (Grazing angle is equal to 90° minus angle of incidence). The Y-axis of the graph shows absorbance units per meter of length of the light pipe. Curve A shows relatively high absorbance using a light pipe diameter of 8 mm; curve B shows lower absorbance using a light pipe diameter of 16 mm; and curve C shows the absorbance using a light pipe diameter of 32 mm. For a given divergence angle, the amount of absorbance is inversely proportional to the diameter (except at 0° grazing angle).

Figure 4:
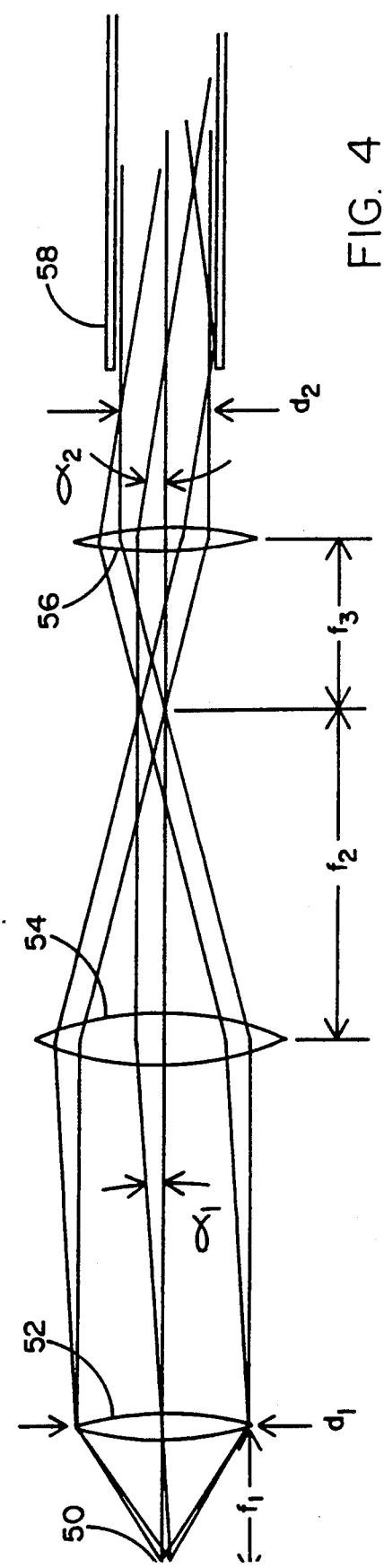
FIG. 4 is an optical diagram of a constant throughput optical system.

FIG. 4 is an optical diagram which illustrates the relationship between beam divergence and beam diameter for a constant throughput optical system. In the figure, lenses are shown as the optical elements, for the sake of simplicity. In a typical infrared system, parabolic mirrors are used rather than lenses. But the general conclusions apply to either arrangement, although the mirrors do cause some departure from ideal conditions (more complicated aberrations).

In discussing FIG. 4, it is assumed that the maximum throughput of the system is determined by the detector optics rather than by the interferometer or sampling system. This is most often the case when working at low spectral resolutions. Note that throughput is a measure of the total amount of optical power that can be transmitted by a system. It is equal to the area of the optical beam times the solid angle beam divergence (taken in a plane where the beam has a uniform intensity distribution).

In FIG. 4, r is the radius of the detector 50, $f_1$ is the focal length of the detector lens 52, and $d_1$ is the diameter of this lens. If the detector is located in the focal plane of the lens, the detector will "see" a bundle of radiation entering the lens which has a half angle divergence equal to $alpha_1$, where $\tan alpha_1 = r/f_1$. For small angles, the solid angle beam divergence will equal $3.1416(r/f_1)^2$; and the throughput in the detector plane will be approximately $3.1416(alpha_1 d_1)^2$.

The second and third optical elements (lenses 54 and 56) of FIG. 4 constitute a beam condenser (or expander) intended to match the diameter of the detector's field of view to that of a light guide 58. Lens 54 has a focal length of $f_2$; and lens 56 has a focal length of $f_3$. Ideally the end of the light guide would be located in the plane indicated by diameter $d_2$, where there are both a minimum beam diameter and a uniform distribution of ray angles and positions. From the construction shown in FIG. 4, it can be seen that the following conditions apply:

$$d_2 = d_1(f_3/f_2) \text{ and } alpha_2 = alpha_1(f_2/f_3)$$

From this it can be seen that the throughput in plane $d_2$ will be the same as in the plane of detector lens 50, and that the divergence angle will be inversely proportional to the beam diameter $d_2$.

By using an appropriate beam condenser (or expander), the diameter of the beam can always be matched to that of an available light pipe, while preserving throughput. Clearly there is an advantage to using a larger light guide, since, in matching the beam diameter to the light guide diameter the divergence angle is automatically reduced.

FIG. 4 also illustrates the advantage of having the smallest possible detector 50, i.e., the lowest value of r. It can be seen that the use of a relatively small area detector can be advantageous, since this will limit the divergence angle for a given size light guide. Consider the following example: Assume a convenient light guide diameter $d_2$ of 32 mm, a detector lens diameter $d_1$ matching that diameter, a focal length $f_1$ of 20 mm, and a detector radius r of 0.5 mm. For this case, the maximum divergence in the light guide will be 1.43 degrees; and the median ray divergence will be approximately 1 degree. If the detector radius r is reduced to 0.25 mm, the maximum ray divergence will be 0.71 degrees and the median ray divergence will be about 0.5 degree. This difference can be particularly significant when attention is directed to the affect which the choice of coating material for the light pipe reflecting surface has on the angle of minimum reflectance.

Figure 5:
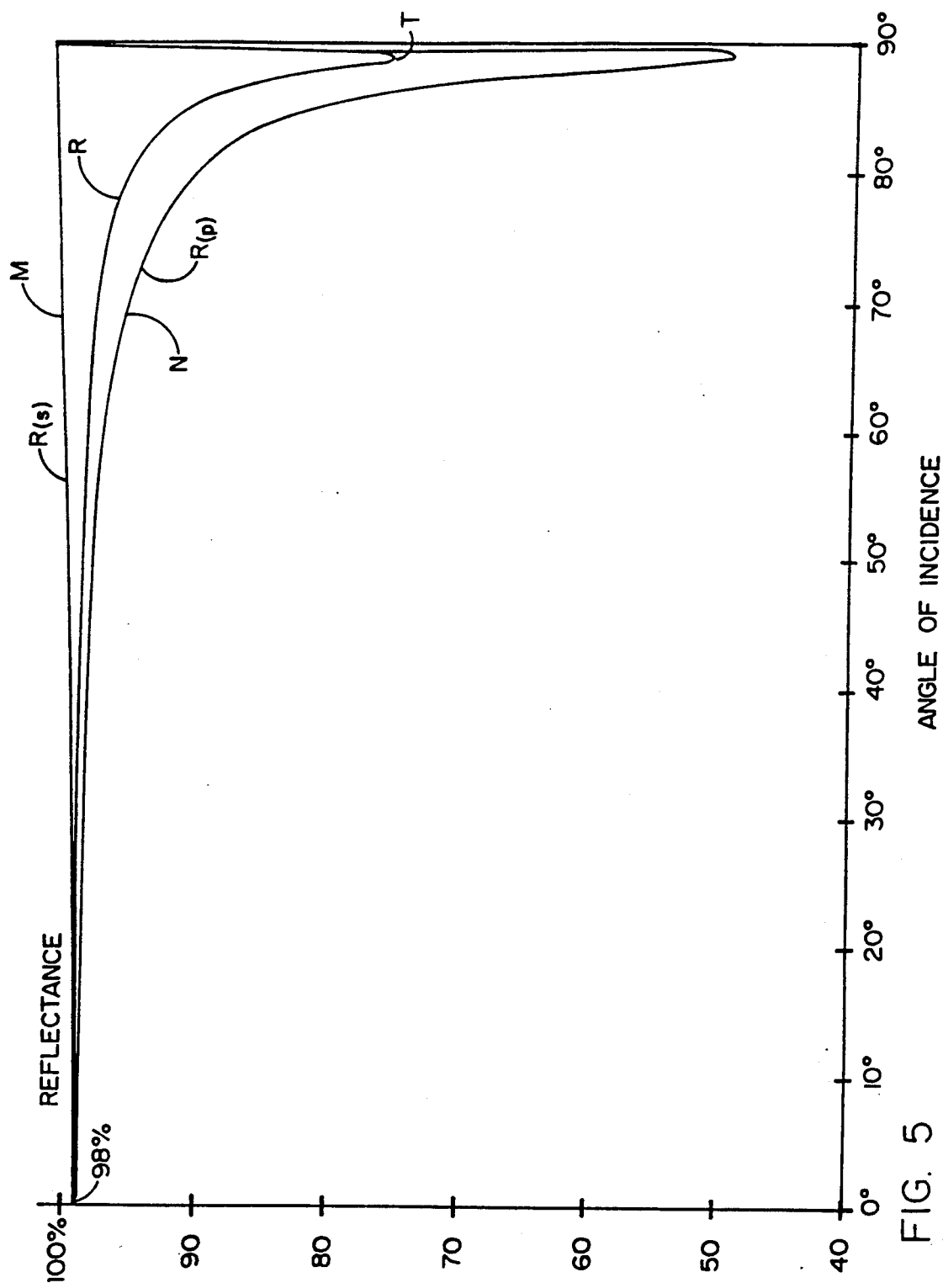
FIG. 5 is a graph showing a set of reflectance curves of aluminum.

FIG. 5 shows a set of reflectance curves for aluminum, with reflectance (Y-axis) plotted against angle of incidence (X-axis). The line M shows the reflectance of rays in the "s" polarization state (perpendicular to the plane of incidence). The line N shows the reflectance of rays in the "p" polarization state (parallel to the plane of incidence). And the line R shows the average of lines M and N, representing the probable actual reflectance. As the figure shows, the reflectance (line M) for the "s" polarization state increases monotonically for increasing incidence angle, while the reflectance (line N) for the "p" state undergoes a deep dip with a minimum very near to grazing incidence. This would not be a serious problem if each ray remained either an "s" ray or a "p" ray on successive reflections. However, all rays will be to some extent skew rays, (i.e., they will make some angle with the nearest plane containing the axis of the light pipe). And skew rays tend to spiral around the pipe, so that their plane of incidence changes on each reflection. Thus, it is safest to assume that, after a few reflections, the "s" and "p" rays will be scrambled. It should therefore be assumed that the actual reflectance is equal to the average of the "s" and "p" reflectance. This is the middle curve (line R) of the figure.

Both lines N and R (representing reflectance values) rise sharply just before reaching the 0° grazing angle. The minimum total reflectance occurs at point T on line R. The very small grazing angle between 0° and the minimum reflectance point T is a potential "window" of high reflectance efficiency (low absorbance).

Applicant has obtained surprising results from comparisons of locations of the point of lowest total reflectance of various potential reflective coating materials. A material which has very high reflectance values at normal instance, such as aluminum, may be a less desirable light pipe coating than a material having lower reflectance values at normal incidence but a larger acceptable grazing angle, such as nickel. Because a larger acceptable grazing angle of the coating will tolerate larger divergence angles of the rays in the radiation beam, significant throughput improvements (reduced absorbance losses) are obtainable.

The curves in FIG. 5 were generated by writing a computer program to give reflectance as a function of angle of incidence and polarization state, using the Fresnel laws of reflection. The curves given are for aluminum at a wavelength of 10$\mu$. The inputs to the program were the real and imaginary parts of the index of refraction, "n" and "k" for this material (n=26, k=67). For these values, the minimum reflectance falls within one degree of grazing incidence. This makes it quite difficult to confine the radiation to angles for which the reflectance will be high.

Figure 6:
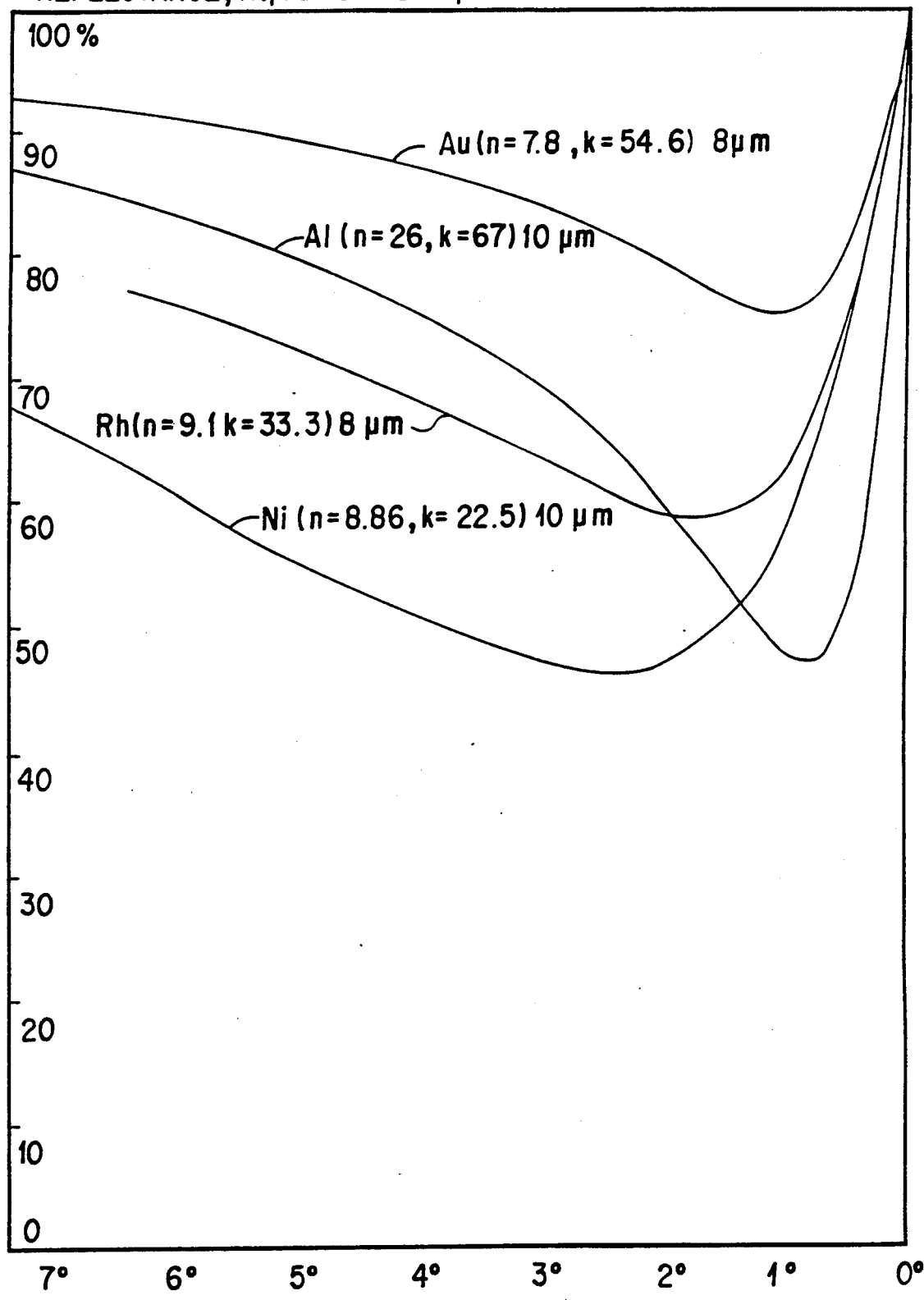
FIG. 6 is a graph comparing the "p" state reflectance curves of four metals.

FIG. 6 compares the "p" state reflectance of four metals—gold, aluminum, rhodium, and nickel—at angles near grazing incidence. These metals share the characteristic of being relatively immune to degradation with time, compared to other materials that might be used in light pipes. It is clear from this figure that gold would be an excellent material for the light guide coatings. However, it is both very expensive and difficult to apply as a coating on the inside of long tubes.

Comparing the four curves of FIG. 6, it can be seen that the ideal light guide optical material would be one with a high value of "k" and a low value of "n". Aluminum, for example, with high values of both "k" and "n", is a good reflector for angles far from grazing, but a poor reflector for angles near grazing. This is due to the fact that a high value of "n" gives rise to a reflectance dip which is both quite deep and located very close to grazing incidence.

Rhodium and nickel are only fair reflectors at angles near normal incidence, due to their low values of "k". However, both of these materials have relatively low values of "n", with the result that the dip in their reflectance is displaced away from grazing. Therefore, they are both considerably better reflectors than aluminum at angles very near grazing. In addition, nickel is inexpensive and can be easily coated on the inside of metallic tubing. These are important factors for light pipes of desirable lengths, e.g., in the range of five to ten feet.

It is apparent from both FIGS. 5 and 6 that, once the grazing angle of the radiation in the light pipe is less than the value for minimum reflectance (the lowest point in each curve), the reflectance will increase dramatically for further reductions in angle. Therefore, to the extent that the angle of divergence of radiation in the pipe is below the grazing angle at which minimum reflectance occurs, the throughput will be disproportionately improved.

Figure 7:
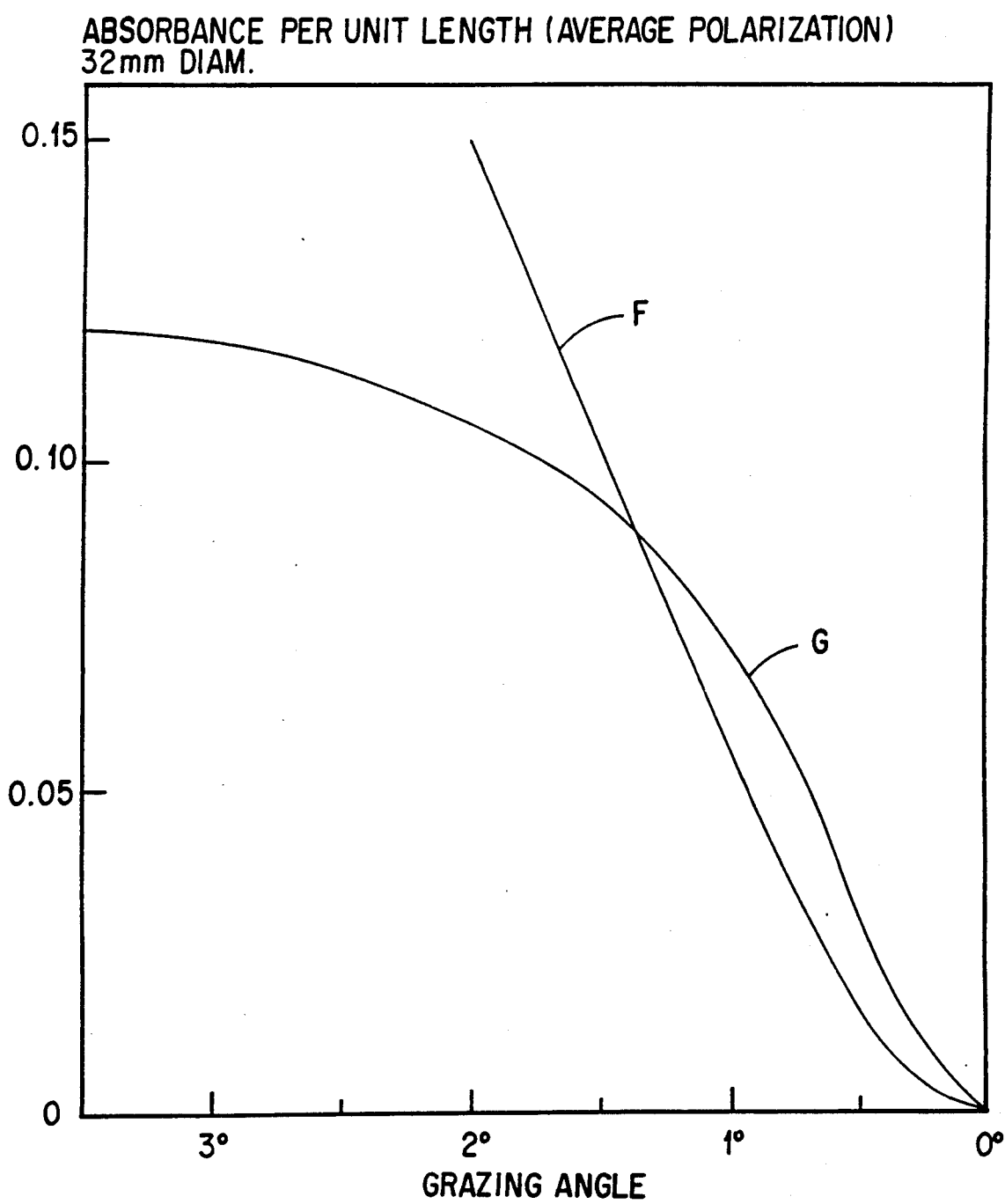
FIG. 7 is a graph showing the absorbance per unit length of 32 mm light pipes coated with aluminum and nickel.

FIG. 7 gives the absorbance per unit length of 32 mm diameter light guides coated, respectively, with aluminum and nickel. Absorbance is shown on the Y-axis and the grazing angle is shown on the X-axis. At angles within about 0.7 degrees of grazing, the absorbance of the nickel coated guide (curve F) is typically on half of that of the aluminum coated guide (curve G). The importance of this difference can be appreciated by considering specific examples. For example, if a pair of equal length light guides have a length selected to give absorbance values of 0.5 and 1.0 for nickel and aluminum, respectively, the transmittances will be 32% for nickel and 10% for aluminum. If the length is then doubled, the absorbance values would be 1.0 for nickel and 2.0 for aluminum; and their respective transmittances would be 10% and 1%.

Referring back to the example showing the benefits of having a small diameter detector, note that a detector having a radius of 0.25 mm would permit a maximum ray divergence angle of 0.71 degrees, and a median ray divergence angle of about 0.5 degrees. With a nickel coating, the reduction of the detector radius from 0.5 mm to 0.25 mm will result in a decrease in light absorbance per unit length by a factor of 3.4 (in the case of the median ray).

The above factors would not be as valuable if the noise equivalent power (NEP) of the infrared detector were independent of the its area, since the smaller detector would have only one fourth the collecting area. However, the NEP of cooled Mercury Cadmium Telluride (HgCdTe) detectors generally decreases (improves) with reduced area. For this reason, those working with GC/IR light guides typically use small (0.5 mm diameter) detectors.

Room temperature pyroelectric detectors are generally thought to have an NEP which is independent of diameter below about 1 mm. However, applicant believes that a small area detector will have an improved NEP if it is heated to near its Curie temperature. Thus the benefits discussed above may apply even with a room temperature detector.

In a practical light guide system, it is often desirable to divert the beam in various directions. This can be done quite effectively, without materially degrading the requirement that the rays stay very close to grazing incidence, if a structure is used which maintains the mirror and light guides in proper alignment as the mirror rotates around the axis of either guide. Such a structure is shown in FIG. 8.

Figure 8:
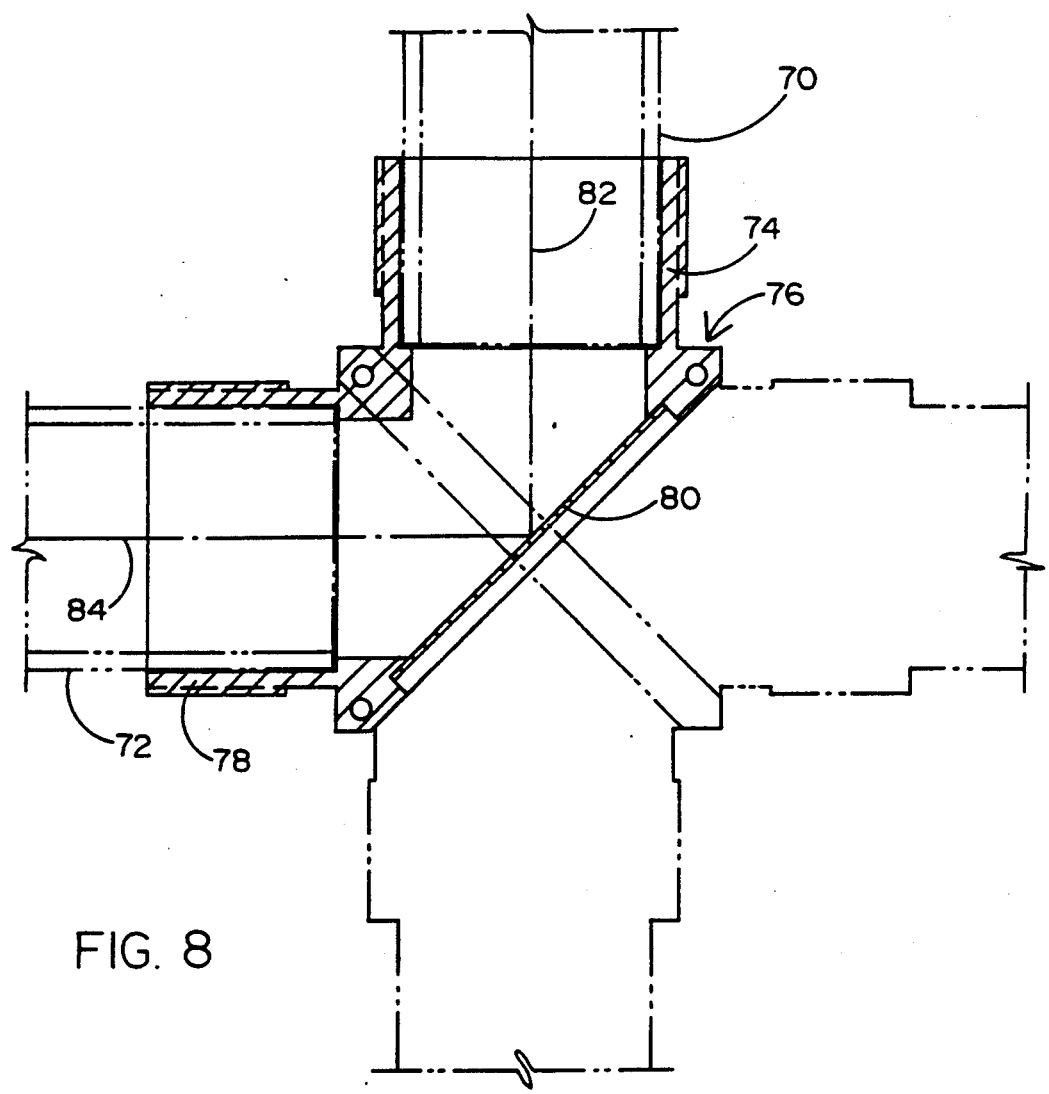
FIG. 8 shows a rotary joint connecting two light pipes, which are rotatable around one another without loss of efficiency.

In FIG. 8, a first light pipe 70 is at right angles to a second light pipe 72. Pipe 70 fits into a first sleeve 74 of a fitting 76; and pipe 72 fits into a second sleeve 78 of fitting 76. Fitting 76 has an opening in which a flat mirror 80 is mounted. With the mirror in place collimated radiation centered on an axis 82 is reflected so as to be centered on an axis 84.

The direction of either light pipe may be changed by rotating the sleeve of fitting 76 around the end of the other light pipe without causing misalignment of the collimated radiation paths 82 and 84.

From the foregoing description, it will be apparent that the apparatus disclosed in this application will provide the significant functional benefits summarized in the introductory portion of the specification.

The following claims are intended not only to cover the specific embodiments disclosed, but also to cover the inventive concepts explained herein with the maximum breadth and comprehensiveness permitted by the prior art.

What is claimed is:

1. A radiation transmission system, for a spectrometer system having a source which provides pre-sample radiation and a detector which receives post-sample radiation, comprising:
    means for causing a substantial portion of the radiation to be in the form of a collimated beam; and
    a hollow light pipe for the collimated radiation beam having a longitudinal passage therethrough whose axis of symmetry coincides with the axis of symmetry of the collimated beam, whose cross-sectional area is substantially equal to the cross-sectional area of the collimated beam, and whose inner surface is highly reflective.

2. The radiation transmission system of claim 1 in which the hollow light pipe length is at least 25 times the square root of the light pipe cross-sectional area.

3. The radiation transmission system of claim 1 in which the collimated beam and the hollow light pipe passage are cylindrical, and the ratio of the length of the light pipe to its diameter is at least 25.

4. The radiation transmission system of claim 3 which comprises:
    optical elements external to the hollow light pipe so arranged as to insure that most of the radiation in the collimated beam has an angular divergence no greater than 1.5° from the light pipe axis.

5. The radiation transmission system of claim 1 which comprises:
    optical elements external to the hollow light pipe so arranged as to insure that most of the radiation in the collimated beam has an angular divergence no greater than 1.5° from the light pipe axis.

6. The radiation transmission system of claim 1 which comprises:
    optical elements external to the hollow light pipe so arranged as to reduce the angular divergence of the collimated radiation to the lowest value consistent with the required radiation throughout of the system.

7. The radiation transmission system of claim 6 which also comprises:
    coating material on the wall of the longitudinal passage whose point of minimum reflectance occurs at a grazing angle not substantially less than the angular divergence of the collimated radiation.

8. The radiation transmission system of claim 6 which also comprises:
    coating material on the wall of the longitudinal passage whose point of minimum reflectance occurs at a grazing angle greater than the angular divergence of most of the collimated radiation.

9. The radiation transmission system of claim 6 in which the angular divergence of the collimated radiation is such that the median ray divergence is no greater than approximately 1° from the axis of the hollow light pipe.

10. The radiation transmission system of claim 9 which comprises:
    coating material on the wall of the longitudinal passage whose point of minimum reflectance occurs at a grazing angle larger than most of the angular divergence of the collimated radiation.

11. The radiation transmission system of claim 9 which comprises:
    coating material on the wall of the longitudinal passage whose point of minimum reflectance occurs at a grazing angle larger than 1°.

12. The radiation transmission system of claim 11 in which the coating material is nickel.

13. The radiation transmission system of claim 1 which comprises:
    coating material on the wall of the longitudinal passage whose average reflectance at a radiation grazing angle of approximately 0.5° is at least approximately 70%.

14. The radiation transmission system of claim 1, which also comprises:
    coating material on the wall of the longitudinal passage whose point of minimum reflectance occurs at a grazing angle not less than 1°.

15. The radiation transmission system of claim 1 which comprises:
    optical elements external to the hollow light pipe so arranged as to insure that most of the radiation in the light pipe has a median ray angular divergence from the axis of the light pipe which is less than 1.5°.

16. The radiation transmission system of claim 15 which also comprises:
    coating material on the wall of the longitudinal passage whose minimum reflectance point occurs at a grazing angle no less than the median ray angular divergence.

17. The radiation transmission system of claim 1 in which the light pipe comprises:
    a first hollow light pipe element;
    a second hollow light pipe element extending at an angle to the first light pipe element; and
    a fitting which interconnects the first and second light pipe elements and which has a flat mirror arranged to reflect radiation from the first light pipe element into the second light pipe element without altering the collimated beam;
    the fitting and the first and second light pipe elements being so joined that either light pipe element may be rotated with respect to the fitting in order to permit changing the direction of the other light pipe element without affecting the collimated beam.

* * * * *

UNITED STATES PATENT AND TRADEMARK OFFICE
CERTIFICATE OF CORRECTION

PATENT NO. : 5,054,869
DATED : October 8, 1991
INVENTOR(S) : Walter M. Doyle

It is certified that error appears in the above-identified patent and that said Letters Patent is hereby corrected as shown below:

Column 2, line 29: "particularly" should be -- particular --.

Column 4, line 29: The mathematical expression should be -- $3.1416(r/f_1)^2$ --.

Column 4, line 30: The mathematical expression should be -- $3.1416 (alpha_1\ d_1/2)^2$ --.

Column 6, line 34: "on" should be -- one --.

Column 8, line 51, "no" should be --not--.

Signed and Sealed this

Ninth Day of March, 1993

*Attest:*

STEPHEN G. KUNIN

*Attesting Officer*    *Acting Commissioner of Patents and Trademarks*